United States Patent [19]

Berg et al.

[11] 4,375,462
[45] Mar. 1, 1983

[54] A-32724 ANTIBIOTICS AND PROCESS FOR PRODUCTION THEREOF

[75] Inventors: David H. Berg, Greenfield; Marvin M. Hoehn, Indianapolis, both of Ind.

[73] Assignee: Eli Lilly and Company, Indianapolis, Ind.

[21] Appl. No.: 302,909

[22] Filed: Sep. 16, 1981

[51] Int. Cl.$^3$ .......................... A61K 35/00; C12P 1/02
[52] U.S. Cl. .................................... 424/117; 435/171; 424/115
[58] Field of Search .......................... 435/171; 424/117

[56] References Cited
PUBLICATIONS

Kumagai et al., *J. Antibiot.* 24(12), 870–875, (1971).
Aoyagi et al., *J. Antibiot.* 24(12), 860–869, (1971).
Yaginuma et al., *J. Antibiot.* 33(3), 337–341, (1980).

*Primary Examiner*—Jerome D. Goldberg
*Attorney, Agent, or Firm*—Dwight E. Morrison; Arthur R. Whale

[57] ABSTRACT

Antibiotic A-32724 complex, comprising microbiologically-active, related factors A, B and C, is produced by submerged, aerobic fermentation of a strain of *Chaetomella raphigera* Swift NRRL 12331. The A-32724 antibiotics are closely related antibiotics. The individual A-32724 factors are separated by chromatography. In addition to their antibacterial activity, the A-32724 factors inhibit certain enzymes and exhibit antihypertensive properties.

2 Claims, 3 Drawing Figures

A-32724 ANTIBIOTICS AND PROCESS FOR PRODUCTION THEREOF

BACKGROUND OF THE INVENTION

This invention relates to a new group of antibiotics which have activity as antibacterial, antifungal, and anti-hypertensive agents, as well as being inhibitors of certain enzymes. An enzyme is an organic compound, frequently a protein, capable of producing, by catalytic action, the transformation of some other compound or compounds.

In addition, all of the antibiotics of the group are active as antihypertensive agents.

In the literature, Kumagai et al., *J. Antibiot.* 24(12), 870–875 (1971), describe the chemistry of an enzyme inhibitor, panosialin, produced by *Streptomyces*. These authors show that panosialin, which inhibits sialidase, acid phosphatase, and polygalacturonase, is a mixture of 5-alkylbenzene-1,3-disulfates. The structures of the three major components are identified as: 5-isopentadecylbenzene-1,3-disulfate; 5-n-pentadecylbenzene-1,3-disulfate; and 5-isohexadecylbenzene-1,3-disulfate. The biological activity, isolation and characterization of panosialin are described by Aoyagi et al., *J. Antibiot.* 24(12), 860–869 (1971).

Also in the literature, Yaginuma et al., *J. Antibiot.* 33(3), 337–341 (1980), describe the isolation, physicochemical properties, and biological characterizations of two water-soluble, acidic, sulfur-containing substances, identified as M4854-I and M4854-II, which are obtained from a culture filtrate of *Chaetomella raphigera* M4854. The substances have demonstrated enzyme-inhibitory activity against a number of $\beta$-lactamases.

Pharmaceutically-active substances useful for the treatment of hypertension, bacterial and fungal caused infections and diseases have been the subject of intensive research for many years. Such substances are of great benefit to mankind.

SUMMARY OF THE INVENTION

This invention relates to the A-32724 antibiotic complex comprising several factors, including individual factors A, B, and C. This complex is produced by culturing a hitherto undescribed strain of *Chaetomella raphigera* Swift NRRL 12331. These A-32724 antibiotics inhibit certain enzymes, and exhibit antihypertensive properties.

DESCRIPTION OF THE DRAWINGS

Infrared absorption spectra of A-32724 factors A, B and C are presented in the drawings as follows.

DETAILED DESCRIPTION

Figure 1:
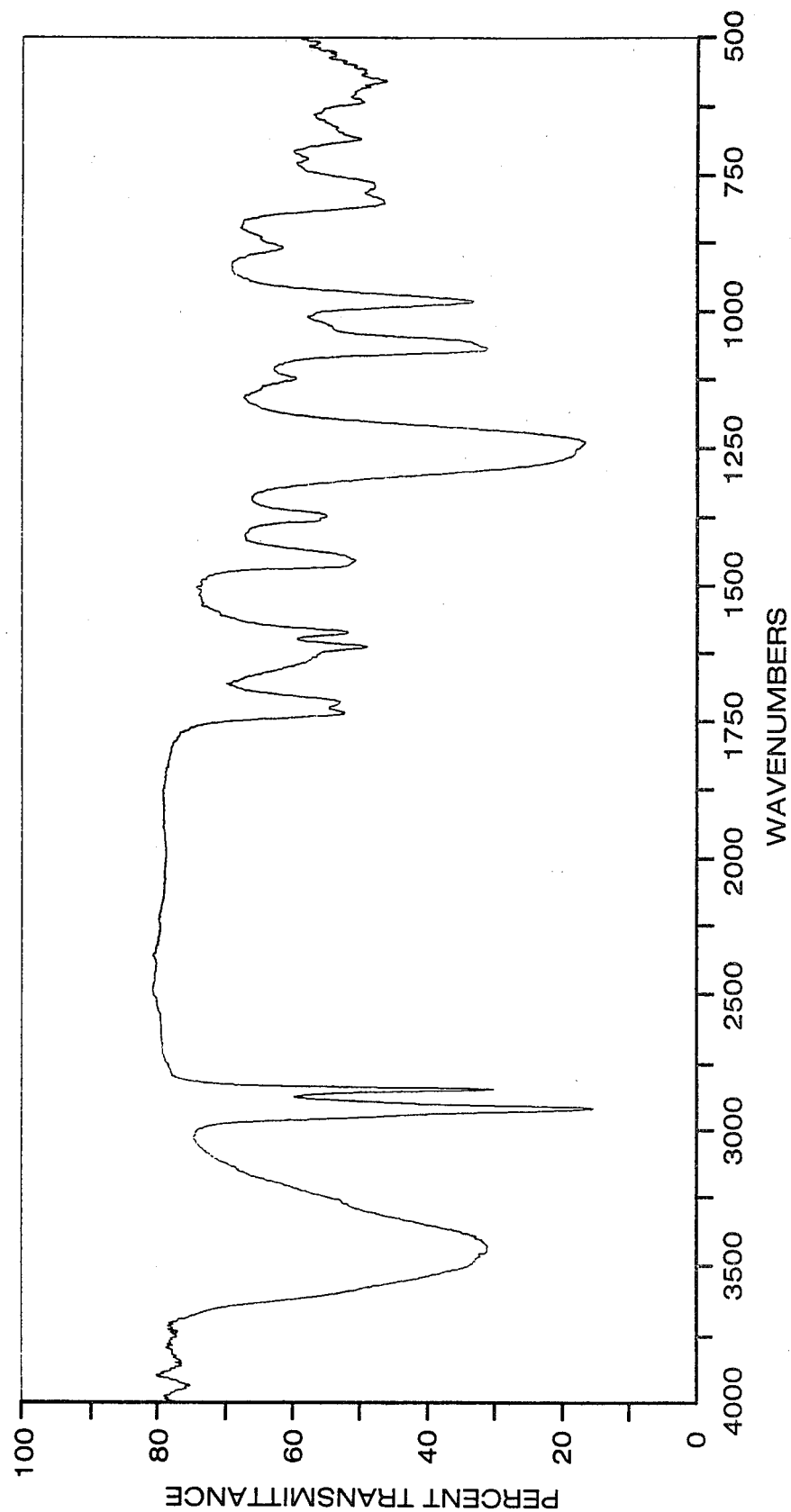
FIG. 1—A-32724 factor A (KBr pellet)
FIG. 2—A-32724 factor B (KBr pellet)
FIG. 3—A-32724 factor C (KBr pellet)

This invention relates to antibiotic substances. In particular, this invention relates to an antibiotic complex, designated the A-32724 complex, which comprises several factors, including individual factors A, B and C. This complex is produced by culturing a hitherto undescribed strain of *Chaetomella raphigera* Swift NRRL 12331, which is also designated herein as culture A-32724.

The term "complex", as used in the fermentation art and in this specification, refers to a mixture of co-produced individual antibiotic factors. As will be recognized by those familiar with antibiotic production by fermentation, the number and ratio of the individual factors produced in an antibiotic complex will vary, depending upon the fermentation conditions and the strain used.

Characterization of the A-32724 Microorganism

A-32724 is a species of Chaetomella in the order of Sphaeropsidales of the Deuteromycetes, the diagnosis being based upon the pycnidial or imperfect state. No perfect state is known. Two characteristics always associated with Chaetomella distinguish the genus from Amerosporium. In Chaetomella, conidia are hyaline and the pycnidium exhibits a raphe which is a longitudinal line of thin-walled cells bordered by thick-walled, dark brown cells along the upper pycnidial wall. The raphe generally behaves as an ostiole through which conidia dehisce. In more mature pycnidia the raphe is not as easily discerned, due to the darkening of the pycnidial walls, and the raphe may then appear as a dark ridge. In Amerosporium there is no raphe and conidia are in green shades.

Culture A-32724 is classified as a strain of *Chaetomella raphigera* Swift, based on direct observations of culture A-32724, and comparison of its characteristics with descriptions of *Chaetomella oblonga*, *Chaetomella circinoseta*, *Chaetomella raphigera*, and *Chaetomella acutiseta*, reported by A. C. Stolk, "The Genus Chaetomella Fuckel", *Transactions of the British Mycological Society* 46(3), 409–425 (1963); and by B. C. Sutton et al., "Revision of Chaetomella, and Comments upon Vermiculariopsia and Thyriochaetum", *Transactions of the British Mycological Society* 66(2), 297–303 (1976).

A-32724 grown on malt extract agar produces a colony up to 50 mm. in diameter in 12 days, which colony is zonate, velutinous, and a beige to grayish mat. Pycnidia are randomly scattered or occasionally zonate.

The pycnidia are superficial on short, fibrous stripes, subglobose to ellipsoid or reinforme. The pycnidia may collapse when drying, are at first hyaline, and then range from brown to black. The stripe originates as a synnematous or fibrous bundle, then swells distally as the pycnidium forms. The pycnidium is composed of three distinct layers of cells: an outer layer, which appears radially fibrous in early stages, and hyaline; a middle layer of pseudoparenchyma, which becomes brown to black with age; and a hyaline inner layer of pseudoparenchyma, from which conidiophores arise. The outer surface of each pycnidium is adorned with randomly scattered setae. Mature pycnidia in a lateral view measure from about 187 to about 335$\mu$ long by from about 148 to about 234$\mu$ wide, with an average size of about 266×184$\mu$.

The conidiophores are filiform, irregularly branched, hyaline, and they terminate in long flexous filaments measuring up to 80$\mu$ in length. Conidiogenous cells are monophialidic, discrete, determinant, and may be randomly distributed, although they are frequently opposed. Conidia are terminally produced from phialides, and are hyaline, frequently guttulate, aseptate, fusiform to allantoid, or boat-shaped. The conidia range from about 5.4 to about 7.1$\mu$ long and from about 1.6 to about 2.0$\mu$ wide, averaging about 6.0×1.7$\mu$. The conidia dehisce in a matrix of cream-colored mucous.

In A-32724, setae occur in two forms, identified as straight (Type I), or as apically hamate (Type II). Type I setae are described in the literature as the oblonga type, after the Chaetomella lectotype *Chaetomella oblonga* Fuckel. See Sutton et al., supra.

In the A-32724 culture, some of the setae are straight and club-shaped, and the swollen terminal cell is subhyaline. The basal cell, which is embedded in pseudoparenchyma, is irregularly swollen, and may often appear as a modified foot-cell. The basal cell is about $5.75\mu$ wide at the pycnidial surface; the middle cells are about $3.4\mu$ wide; and the apical cell is about $5.3\mu$ wide. The apical cell is generally obtuse, but sometimes may be acute. An apical cell ranges in length from about $44.5\mu$ to about $66.6\mu$, and averages about $51.6\mu$ in length.

The second type of setae in A-32724 are apically hamate, but never more than one complete turn. The tip is obtuse and occasionally acute. The basal cell is similar to those in the first type of setae described above. However, development of septa in this second type of setae occurs later than in the first type of setae. Pigmentation of the second type of setae is similar to that of the first type of setae. The second type of setae ranges in length from about 58.2 to about $92\mu$, with an average length of about $77.4\mu$.

In the A-32724 culture, a second conidial fruiting structure, the spordochium, arises from a synnematous bundle of hyphae which is frequently constricted centrally, and appears as a fibrous hourglass stipe. Conidia are similar to those of the pycnidium and also develop in a cream-colored slime that darkens with age. Sporodochia are frequently setaceous.

On oatmeal agar, A-32724 achieves colony diameters of 65 mm in 12 days. The colony is irregularly sectored and develops radial folds along which pycnidia are first observed. As the colony ages, pycnidia occur singly or in clusters at random over the entire surface. The colony surface initially is white, becoming beige, is flat and velutinous. Pycnidia are most abundant when growth virtually ceases and are emphasized by a changing mycelial surface which becomes appressed and nearly void of free-standing aerial hyphae. The periphery is irregularly crenate to lobate. On the reverse side, the colony is yellowish white, becoming light brown with age.

Pycnidia are stipitate, subglobose to reniform, setaceous, and carbonaceous. They are colorless at first, then evolve through shades of brown to black. The characteristics of the longitudinal raphe are most easily discerned in the young colorless to light brown pycnidia where the thin-walled colorless line of raphe cells become outlined with thick-walled darker brown cells.

In the mature, black pycnidium, the raphe appears as a sharp, unbroken longitudinal ridge across the upper pycnidial surface. The wall of the dried and aged pycnidium frequently collapses, emphasizing the lateral reniform appearance. Pycnidia on oatmeal agar are from 233 to $319\mu$ long, are from 156 to $217\mu$ wide, and average $272\times179\mu$. As on malt extract agar, setae are light brown, 2-6 celled, and occur in two forms. Both types may be described as on malt extract agar. Type I ranges in length from 44 to $55\mu$, averaging $51\mu$. They are $5\mu$ wide at the pycnidial surface, $3.4\mu$ wide in their mid-regions, and $5\mu$ wide in the apical, clavate cell. Type II, apically hamate setae, are from $42-74\mu$ long, average $50\mu$, and are $3-3.4\mu$ wide. Type I setae have, therefore, approximately the same dimensions as those of malt extract agar. Type II setae are possibly shorter than those reported on malt extract agar, but their dimensions fall within the range described in the literature.

On potato-dextrose agar, A-32724 achieves a diameter of 50 mm in 12 days. Aerial hyphae predominate in approximately a 30 mm diameter zone in the center of the colony. This portion of the mycelium is flat and velutinous and is, at first, white but evolves to light gray with age. Sectoring within the colony causes an irregularly lobate appearance which becomes emphasized by the development of brown to black pycnidia and more numerous sporodochia. Interlobal mycelial areas are appressed and virtually free of pycnidia, with limited sporodochia present. A marginal 5 mm wide band of the mycelium is submerged.

Characteristics of pycnidia on potato-dextrose agar are as described on malt extract and oatmeal agars. The rate of pycnidial elaboration on this agar increases as the agar dries. These pycnidia are from 218 to $288\mu$ long and from 140 to $210\mu$ wide, averaging $265\times180\mu$. Clavate setae are from 38 to $52\mu$ long, and average $42\mu$ in length. Hamate setae are from 46 to $70\mu$, long, averaging $58\mu$ long. The diameters of each type are compatible with those described on malt extract and oatmeal agars. The morphology and dimensions of conidiophores, phialides, and conidia on oatmeal and potato-dextrose agars are as described on malt extract agar.

Sporodochia are similarly expressed on all three media, the development of the sporodochia being enhanced by excessive moisture. For this reason there is a greater expression of sporodochia over pycnidia on potato-dextrose agar which tends to be more moist than malt extract and oatmeal agars. Sporodochia may vary widely in all dimensions and on all 3 agars, as previously described. The upper conidia bearing surface is always marginally adorned with setae which are primarily clavate. Conidia are comparable to those of the pycnidium. Although a typical anamorphic form of the genus Chaetomella, the sporodochium is not a significant factor in species identification.

Since A-32724 possesses both Type I and Type II setae, A-32724 differs from *Chaetomella oblonga*, which has only Type I setae. The setae of A-32724 also differs from those of *Chaetomella circinoseta*, since *C. circinoseta* has two types of setae, one of which is conspicuously spiraled at its apex, with one to four coils and accuminate tips. Such setae are up to 12 septate and may be up to $900\mu$ long. The second type of setae of *C. circinoseta* is clavate at the apex, and measures $60-180\mu$ in length. Both types of setae of *C. circinoseta* are typically longer and more complex than the setae of A-32724. In addition, the conidia in *C. circinoseta* are about twice as long as the conidia of A-32724. The setae and the conidia help distinguish A-32724 from other Chaetomella species.

The morphology of the pycnidia and its various components, including the setae, conidiogenous cells, and pycnidiospores for culture A-32724 on all three media are compatible with each other and with the descriptions in the literature cited above.

The *Chaetomella raphigera* Swift culture which is useful for the production of the A-32724 antibiotics was initially isolated from a soil sample collected in Curacao, Netherlands Antilles, and has been deposited and made a part of the stock culture collection of the Northern Regional Research Center, U.S. Department of Agriculture, Agricultural Research Service, Peoria, Illinois, 61604, from which it is available to the public under the number NRRL 12331.

As is the case with other organisms, the characteristics of the A-32724-producing culture, *Chaetomella*

*raphigera* Swift NRRL 12331, are subject to variation. For example, natural variants, mutants (spontaneous or induced), transconjugants and recombinants (including recombinant DNA or plasmids) of the NRRL 12331 strain, or derived from this strain, which produce the A-32724 antibiotics may be used in this invention.

The A-32724 complex contains several individual factors. Those which have been isolated are designated A-32724 factors A, B and C. In discussions of utility, the term "A-32724 antibiotic" will be used, for the sake of brevity, to denote a member selected from the group consisting of A-32724 complex, and A-32724 factors A, B and C.

The A-32724 factors of this invention are structurally related to each other. As many as three antibiotic factors are recovered from the fermentation and are obtained as a mixture, the A-32724 complex. It will be recognized that the ratio of the factors in the A-32724 complex will vary, depending on the fermentation conditions used.

The following paragraphs describe the physical and spectral properties of those A-32724 factors which have thus far been characterized.

A-32724 Factor A

Antibiotic A-32724 Factor A is a white, amorphous powder, melting at about 175°–176° C. (dec.), having a molecular weight of about 738, and an empirical formula of $C_{33}H_{56}O_{11}S_2Na_2$, determined by combining data from its nuclear magnetic resonance (NMR) spectrum, sulfate determination, and field-desorption and electron-impact mass spectrometry.

A preparation of A-32724 Factor A was subjected to field-desorption mass spectrometry from a solution of 0.2 molar ammonium chloride. Under these conditions, Factor A gave peaks at 694 (free acid); 614 (free acid $-SO_3$); 597 (free acid, $-SO_3$, $-H_2O$, $+H^+$); 517 (free acid, $-2SO_3$, $-H_2O$, $+H^+$); and 456.

The infrared absorption spectrum of A-32724 Factor A (KBr pellet) is shown in the accompanying drawings as FIG. 1. The following distinguishable absorption maxima are observed: 3426 (strong), 2923 (strong), 2852 (strong), 1736 (medium), 1720 (medium), 1616 (medium), 1590 (medium), 1458 (medium), 1383 (shoulder), 1375 (medium weak), 1241 (very strong), 1123 (weak), 1068 (strong), 981 (strong), 884 (weak), 865 (weak), 803 (medium), 771 (medium weak), 722 (weak), 685 (weak), 625 (weak), and 581 cm.$^{-1}$ (weak).

The ultraviolet absorption spectrum of antibiotic A-32724 Factor A in water is not changed by titrating with base or acid, and shows absorption maxima as recorded in Table 1, which follows:

TABLE 1

| UV Spectrophotometry of Antibiotic A-32724 Factor A |
|---|
| $\lambda_{max}$ nm ($\epsilon$) |
| 265 nm (333) |
| 271 nm (sh)[1] (252) |

(sh)[1] = shoulder

The proton magnetic resonance spectrum of antibiotic A-32724 Factor A in DMSO-$d_6$, determined at 100 MHz, using internal TMS as reference, is set forth in Table 2, which follows:

TABLE 2

| Proton Magnetic Resonance Spectrum Of A-32724 Factor A | | |
|---|---|---|
| Resonance Description | Chemical Shift δ, ppm | No. of Protons |
| Triplet | 6.80 | 1 |
| Doublet | 6.74 | 2 |
| Multiplet | 4.67 | 1 |
| Doublet | 4.60 | 1 (exchangeable) |
| Multiplet | 3.40 | 1 |
| Triplet | ~2.5 | Overlapped with solvent |
| Singlet | 1.97 | 3 |
| Multiplet | ~1.5 | } ~42 |
| Broad singlet | 1.23 | |
| Triplet | 0.84 | 3 |

The $^{13}$C NMR spectrum of antibiotic A-32724 Factor A, in DMSO-$d_6$, using internal TMS as reference, shows certain characteristics. The chemical shifts, expressed in parts per million (PPM), are recorded in Table 3, which follows.

TABLE 3

| $^{13}$C NMR Chemical Shifts for A-32724 Factor A | |
|---|---|
| No. | PPM |
| 1 | 170.0 |
| 2 | 153.4[1] |
| 3 | 142.7 |
| 4 | 115.1[1] |
| 5 | 110.4 |
| 6 | 75.8 |
| 7 | 70.8 |
| 8 | 35.2 |
| 9 | 32.2 |
| 10 | 31.2 |
| 11 | 30.9 |
| 12 | 29.3 |
| 13 | 29.0[2] |
| 14 | 28.7[3] |
| 15 | 28.5 |
| 16 | 25.1 |
| 17 | 25.0 |
| 18 | 22.1 |
| 19 | 20.8 |
| 20 | 13.9 |

[1]Represents two carbon atoms and indicates a two-fold symmetry axis through an aromatic ring.
[2]Represents several (the number is indeterminate) carbons of a hydrocarbon chain.
[3]May represent more than one carbon atom.

On the basis of the combined physical/chemical data recorded above, antibiotic A-32724 Factor A is believed to have the following structural formula:

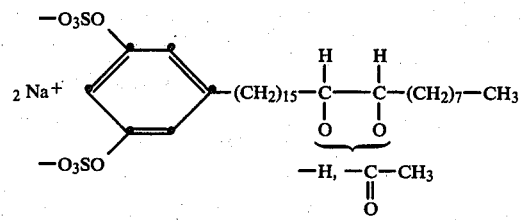

A-32724 Factor B

Antibiotic A-32724 Factor B, is a white, amorphous powder, melting at about 160°–162° C. (dec.), having a molecular weight of about 738, and an empirical formula of $C_{33}H_{56}O_{11}S_2Na_2$, determined by combining data from its NMR spectrum, sulfate determination, and electron-impact and field-desorption mass spectrometry.

A preparation of A-32724 Factor B was subjected to field-desorption mass spectrometry from a solution of 0.2 molar ammonium chloride. Under these conditions, Factor B gave the same peaks as those observed for Factor A under the same treatment.

Figure 2:
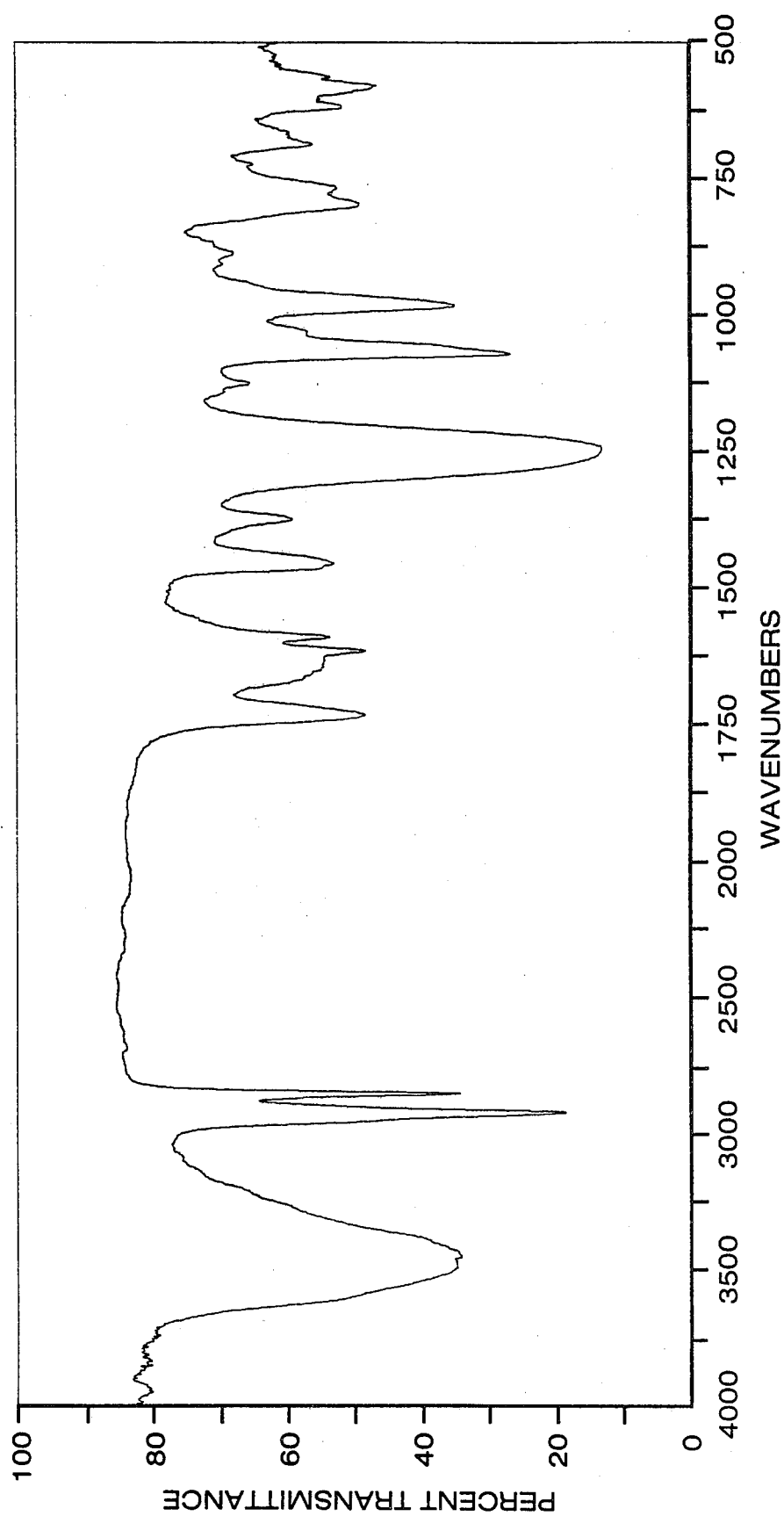

The infrared absorption spectrum of A-32724 Factor B (KBr pellet) is shown in the accompanying drawings as FIG. 2. The following distinguishable absorption maxima are observed: 3468 (strong), 3452 (strong), 2923 (strong), 2853 (strong), 1733 (medium), 1616 (medium), 1591 (medium weak), 1455 (medium), 1376 (weak), 1242 (very strong), 1124 (weak), 1068 (strong), 1032 (shoulder), 980 (strong), 905 (weak), 795 (medium), 767 (medium weak), 721 (weak), 684 (weak), 670 (shoulder), 662 (shoulder), 617 (medium weak), and 579 cm.$^{-1}$ (medium).

The ultraviolet absorption spectrum of antibiotic A-32724 Factor B in water under neutral conditions shows absorption maxima as recorded in Table 4, which follows:

TABLE 4

| UV Spectrophotometry of Antibiotic A-32724 Factor B |
|---|
| $\lambda_{max}$ nm ($\epsilon$) |
| 265 nm (321) |
| 271 nm (sh[1]) (249) |

(sh[1]) = shoulder

The proton magnetic resonance spectrum of antibiotic A-32724 Factor B in DMSO-d$_6$, determined at 100 MHz, using internal TMS as reference, is set forth in Table 5, which follows:

TABLE 5

| Proton Magnetic Resonance Spectrum Of A-32724 Factor B | | |
|---|---|---|
| Resonance Description | Chemical Shift δ, ppm | No. of Protons |
| Triplet | 6.78 | 1 |
| Doublet | 6.73 | 2 |
| Multiplet | 4.95 | 1 |
| Multiplet | 4.08 | 1 |
| Triplet | ~2.5 | Overlapped with solvent |
| Singlet | 1.98 | 3 |
| Multiplet | ~1.5 | ~40 |
| Broad singlet | 1.23 | |
| Triplet | 0.85 | 3 |

The $^{13}$C nuclear magnetic resonance spectrum of antibiotic A-32724 Factor B, in DMSO-d$_6$, using internal TMS as reference, shows certain characteristics. The chemical shifts, expressed in parts per million (PPM), are recorded in Table 6, which follows.

TABLE 6

| $^{13}$C NMR Chemical Shifts for A-32724 Factor B | |
|---|---|
| No. | PPM |
| 1 | 169.8 |
| 2 | 153.4[1] |
| 3 | 142.7 |
| 4 | 115.1[1] |
| 5 | 110.3 |
| 6 | 75.9 |
| 7 | 72.8 |
| 8 | 62.9 |
| 9 | 41.1 |
| 10 | 40.2 |
| 11 | 39.4 |
| 12 | 33.5 |

TABLE 6-continued

| $^{13}$C NMR Chemical Shifts for A-32724 Factor B | |
|---|---|
| No. | PPM |
| 13 | 37.7 |
| 14 | 35.2 |
| 15 | 31.2 |
| 16 | 30.8 |
| 17 | 29.9 |
| 18 | 29.0[2] |
| 19 | 25.0 |
| 20 | 24.5 |
| 21 | 22.0 |
| 22 | 20.7 |
| 23 | 13.9 |
| 24 | 0.0 |

[1] Represents two carbon atoms and indicates a two-fold symmetry axis through an aromatic ring.
[2] Represents several (the number is indeterminate) carbons of a hydrocarbon chain.

Based on the shifts in the NMR spectra, Factor B differs in structure from Factor A in chirality at the two methines, and the factors may also differ in the location of the acetyl group.

A-32724 Factor C

Antibiotic A-32724 Factor C is a white, crystalline material having a melting point of about 185°–186° C.

Figure 3:
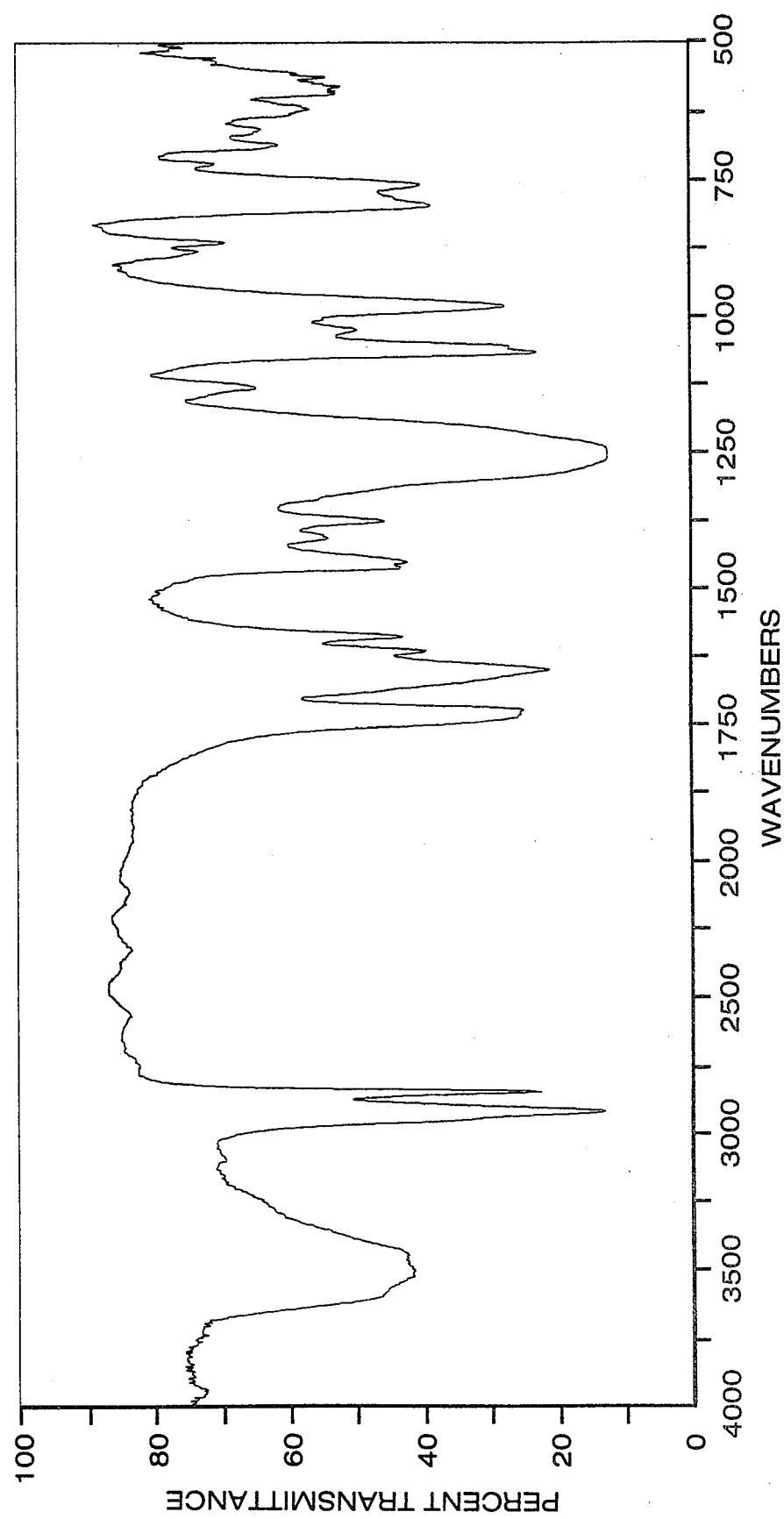

The infrared absorption spectrum of A-32724 Factor C (KBr pellet) is shown in the accompanying drawings as FIG. 3. The following distinguishable absorption maxima are observed: 3498 (medium), 3452 (medium), 2922 (strong), 2851 (strong), 1733 (strong), 1724 (strong), 1652 (strong), 1616 (medium), 1591 (medium), 1465 (medium), 1455 (medium), 1409 (weak), 1378 (medium), 1257 (very strong), 1132 (weak), 1065 (strong), 1054 (shoulder), 1025 (weak), 981 (strong), 880 (weak), 865 (weak), 795 (medium), 721 (weak), 664 (weak), 657 (weak), 620 (weak), 594 (weak), 580 (weak), 563 (weak), and 481 cm.$^{-1}$ (weak).

The proton magnetic resonance spectrum of antibiotic A-32724 Factor C in DMSO-d$_6$, determined at 100 MHz, using internal TMS as reference, is set forth in Table 7, which follows:

TABLE 7

| Proton Magnetic Resonance Spectrum Of A-32724 Factor C | | |
|---|---|---|
| Resonance Description | Chemical Shift δ, ppm | No. of Protons |
| Triplet | 6.80 | 1 |
| Doublet | 6.73 | 2 |
| Multiplet | 4.90 | 2 |
| Triplet | ~2.5 | Overlapped with solvent |
| Singlet | 2.02 | 3 |
| Multiplet | ~1.5 | ~35 |
| Broad singlet | 1.22 | |
| Triplet | 0.85 | 3 |

The ultraviolet absorption spectrum of antibiotic A-32724 Factor C in water shows a UV max=262 nm, $E_{1\ cm}^{1\%}$=3.31.

Factor C is closely related to Factor A, and is transformed into Factor A upon standing in methanol or being warmed in methanol for a period of time.

All the factors are soluble in water and methanol.

Factors A, B and C of the A-32724 complex can be separated and distinguished from one another by employing silica-gel thin-layer chromatography (TLC) and paper chromatography. *Staphylococcus aureus* was the organism employed for the bioautography. The approximate $R_f$ values of factors A, B and C are given in Table 8, which follows.

TABLE 8

| Factor | $R_f$ Solvent System | | | |
|---|---|---|---|---|
| | A[1] | B[1] | C[1] | D[2] |
| A | 0.84 | 0.59 | 0.79 | 0.61 |
| B | 0.81 | 0.35 | 0.47 | 0.36 |
| C | 0.79 | 0.41 | 0.59 | 0.21 |

[1]Paper System
Paper: Whatman No. 1 (untreated)
Solvent:
A = methanol:0.1N HCl (3:1)
B = n-butanol:acetic acid:water (3:1:1)
C = ethyl acetate:acetic acid:water (3:1:1)
[2]Thin Layer System
Medium: Merck, Darmstadt-Silica Gel 60
Solvent: D = acetone:water (19:1)

The electrometric titration of each of factors A, B and C shows in each case a pKa of less than 3. Such a value suggests that each factor will form salts with alkali and alkaline earth metals, as well as ammonium and substituted ammonium ions.

The A-32724 complex is produced by culturing *Chaetomella raphigera* Swift NRRL 12331, or an A-32724-producing variant or mutant thereof, under submerged aerobic fermentation conditions until a substantial level of antibiotic activity is produced. Most of the antibiotic activity is generally found associated with the broth, while lesser amounts of antibiotic activity are present in the mycelia. The A-32724 antibiotic complex is most readily separated from the fermentation mixture by recovery of the fermentation broth by filtration using filter aid. The filter cake, which comprises filter aid and mycelia, is reserved. The filtered broth is extracted at broth pH with an equal volume of a suitable solvent such as n-butanol, and the extract, which contains crude A-32724 complex, is then concentrated to a small volume. The filter cake (reserved above) is extracted with methanol. The extract is concentrated to remove the methanol. The aqueous phase which remains is then extracted with water-saturated n-butanol, and the aqueous layer is discarded.

The methanol extract from the mycelia and the butanol extract from the broth are each concentrated to oils, taken up in methanol and poured into large volumes of isopropyl alcohol. The active precipitates which form are filtered off. The crude A-32724 obtained from the mycelial mass and from the filtered broth and be further purified and separated into individual factors by chromatographic techniques.

A number of different media may be used with *Chaetomella raphigera* Swift NRRL 12331 to produce the A-32724 complex. For economy in production, optimal yield, and ease of product isolation however, certain culture media are preferred. Thus, for example, preferred carbon sources are glucose, sucrose, dextrose, maltose and glycerol. Optimum levels of carbon sources are from about 2 to about 6 percent by weight. Suitable nitrogen sources include peptone and enzyme-hydrolyzed casein.

Essential trace elements necessary for the growth and development of the organism may occur as impurities in other constituents of the media in amounts sufficient to meet the growth and biosynthetic requirements of the organism. However, it may be beneficial to incorporate in the culture media additional soluble nutrient inorganic salts capable of yielding sodium, potassium, magnesium, calcium, ammonium, chloride, carbonate, phosphate, sulfate, nitrate and like ions.

For producing substantial quantities of the A-32724 antibiotic complex, submerged aerobic fermentation in tanks is preferred. However, small quantities of the A-32724 antibiotic complex may be obtained by shake-flask culture. For tank fermentation, it is preferable to use a vegetative inoculum. The vegetative inoculum is prepared by inoculating a small volume of culture medium with the spore form, mycelial fragments, or a lyophilized pellet of the organism to obtain a fresh, actively growing culture of the organism. The vegetative inoculum is then transferred to a larger tank where, after a suitable incubation time, the A-32724 antibiotic complex is produced in optimal yield.

Maximum production of the A-32724 antibiotic complex appears to occur at a temperature of about 25° C.

As is customary in aerobic submerged culture processes, sterile air is dispersed through the culture medium. For efficient growth of the organism, the volume of the air used in the tank production is in the range of from about 0.1 to about 1.5 volumes of air per volume of culture medium per minute (v/v/m), with from about 100 to about 500 RPM agitation. It may be necessary to add small amounts (ie., 0.2 ml/L.) of an antifoam agent such as polypropylene glycol to large-scale fermentation media if foaming becomes a problem.

Antibiotic activity is generally present after about 24 hours and remains present for at least 4 days during the fermentation period. Peak antibiotic production occurs at from about 2 to about 4 days fermentation time.

Production of the A-32724 complex can be monitored during the fermentation by either agar diffusion or turbidimetric methods. Test organisms suitable for use include *Staphylococcus aureus* and *Micrococcus luteus*.

The A-32724 antibiotic complex can be recovered from the fermentation medium by methods used in the art. The major portion of the A-32724 antibiotic complex is present in the fermentation broth. Maximum recovery of the A-32724 antibiotic complex is accomplished, therefore, by an initial filtration to remove the mycelial mass, which is reserved. The filtered broth can be purified by a variety of techniques to give the A-32724 antibiotic complex. A preferred technique involves extraction of the broth at broth pH with a suitable solvent, for example, n-butanol. This extract is then concentrated to remove the solvent and yield an oil. The oil is dissolved several times in a suitable solvent such as methanol, the methanol being removed under vacuum each time to leave a residual oil. The oil is then dissolved in a suitable solvent such as methanol; this solution is poured into a large volume of a solvent in which the A-32724 antibiotics are insoluble, such as isopropyl alcohol. The solid precipitate which forms is recovered by filtration and identified as A-32724 complex.

The mycelial solids are extracted with methanol, and the extracts are concentrated to remove the methanol. The remaining aqueous phase is extracted with n-butanol saturated with water, which extract is then concentrated to a residual oil. This residual oil is treated in the same manner as the oil from the broth, supra, to give additional A-32724 complex.

Separation of the individual A-32724 factors from the A-32724 complex obtained either from the mycelial mass or the filtered broth includes the use of additional adsorption and extraction procedures. Adsorptive materials such as silica gel and the like can be advantageously used.

The A-32724 antibiotics inhibit the growth of certain microorganisms. Thus, the A-32724 antibiotics exhibit activity against both gram-positive and gram-negative organisms, and also show some antifungal activity, as determined in a standard antibiotic disc assay. The results are recorded in Table 9, which follows.

TABLE 9

Antibiotic Spectrum of A-32724 Factors

| Factor | Appln. rate mg/ml | 1 | 2 | 3 | 4 | 5 | 6 |
|--------|-------------------|----|----|----|----|----|----|
| A | 5 | 10 | 11 | 12 | 15 | 15 | — |
| B | 5 | 11 | 15 | — | 20 | 20 | — |
| C | 5 | 10 | 12 | 12 | 17 | 18 | 15 |

1 = *Staphylococcus aureus* ATCC 6538P (G+)
2 = *Micrococcus luteus* ATCC 9341 (G+)
3 = *Saccharomyces cerevisiae* ATCC 2366 (Fungus)
4 = *Serratia marcescens* NRRL B284 (G−)
5 = *Bacillus subtilis* ATCC 6633 (G+), grown on a mineral salts medium
6 = *Escherichia coli* ATCC 4157 (G−), grown on a mineral salts medium All three A-32724 factors have an $LD_{50}$ (i.p., mouse) of about 225 mg./kg.

A-32724 Factors A, B and C have antihypertensive activity. For example, Factor A has been found to lower the blood pressure in spontaneously hypertensive rats approximately 15% at a dosage of 25 mg./kg., when injected intraperitoneally. Factors B and C lower the blood pressure of spontaneously hypertensive rats approximately 15% at a dosage of 50 mg/kg., when injected intraperitoneally. A-32724 Factors A, B and C also have enzyme-inhibiting properties. Thus, for example, Factors A, B and C all inhibit glucosyl transferase with $I_{50}$'s of 75, 90 and 81 μg./ml., respectively.

In order to illustrate more fully the operation of this invention, the following Examples are provided.

EXAMPLE 1

Preparation of First Stage Inoculum

A medium was prepared for use in the agar slant culture of *Chaetomella raphigera* Swift NRRL 12331:

| Ingredient | Amount (g/L.) |
|------------|---------------|
| Glucose | 10.0 |
| Peptone | 5.0 |
| Yeast extract | 3.0 |
| Malt extract | 3.0 |
| $MgSO_4.7H_2O$ | 0.5 |
| KCl | 0.5 |
| $FeSO_4.7H_2O$ | 0.002 |
| Agar | 20.0 |
| Deionized water | q.s. to 1.0 liter |

The pH of the medium was 6.0.

Spores of *Chaetomella raphigera* Swift NRRL 12331 were inoculated on a nutrient agar slant made up of the above-identified ingredients, and the thus-inoculated slant was incubated for about 7 days at a temperature of about 25° C. The mature slant culture was then covered with sterile distilled water and scraped with a sterile tool to loosen the spores and mycelia. One milliliter of the resulting spore suspension was used to inoculate 50 ml. of vegetative medium. An alternate method of providing inoculum for the vegetative medium consisted of substituting a lyophilized pellet for the aqueous spore suspension. Preparation of the spore suspension for lyophilization was similar to preparation of the aqueous spore suspension, except that sterile calf serum was substituted for sterile distilled water. Lyophilized pellets were then prepared in a manner known in the art. Composition of the vegetative medium to be inoculated was as follows:

| Ingredient | Amount (g/L.) |
|------------|---------------|
| Sucrose | 25.0 |
| Molasses | 36.0 |
| Corn-steep liquor | 6.0 |
| Malt extract | 10.0 |
| Enzyme-hydrolyzed casein[1] | 10.0 |
| $K_2HPO_4$ | 2.0 |
| Deionized water | q.s. to 1.0 liter |

[1]N-Z-Case (Humko Sheffield Chemical Co., Memphis, Tennessee.)

After autoclaving, the pH of the medium was 6.5. The vegetative medium was incubated in a 250 ml. wide-mouth Erlenmeyer flask at about 25° C. for about 48 hours on a shaker rotating through an arc 2 inches in diameter at 250 RPM. The resulting culture is used either to inoculate small fermenters (the inoculum being approximately 1% per volume of fermenter medium) or to inoculate a second stage medium having the same composition as the vegetative medium for the production of a larger volume of culture.

Fermentation of A-32724

Incubated second-stage medium (800 ml.) thus prepared was used to inoculate 100 liters of sterile production medium having the following composition:

| Ingredient | Amount (g/L.) |
|------------|---------------|
| Silicone antifoam agent[1] | 0.2 |
| Maltose | 25.0 |
| Glycerol | 20.0 |
| Corn-steep liquor | 2.0 |
| Enzyme-hydrolyzed casein[2] | 5.0 |
| Monosodium glutamate | 10.0 |
| $MgSO_4.7H_2O$ | 0.5 |
| $KH_2PO_4$ | 1.0 |
| Tap water | q.s. to 100.0 liters |

[1]Dow-Corning Antifoam 'A'
[2]N-Z-Amine A (Humko Sheffield Chemical Co., Memphis, Tennessee.)

The pH of the medium was 6.3 before autoclaving and 6.5 after autoclaving.

The inoculated production medium was allowed to ferment in a 165-liter fermentation tank for about 66 hours at a temperature of 25° C. The fermentation medium was aerated with sterile air at the rate of 0.5 v/v/m and was stirred with conventional agitators at 300 RPM.

EXAMPLE 2

Separation of A-32724 Antibiotic

Whole fermentation broth (160 liters), obtained by the procedure described in Example 1, was filtered using 3% filter aid (Hyflo Supercel, a diatomaceous earth, Johns-Manville Products Corporation) in a filter press. The mycelial solids were reserved. The filtered broth was extracted with an equal volume of n-butanol and the aqueous layer was discarded. The n-butanol extract was concentrated to a volume of about 1 liter, diluted with 500 ml. of methanol, and poured into 25 liters (20 volumes) of isopropyl alcohol. The active precipitate which formed was separated by filtration, washed with acetone, and dried in vacuo. It weighed 91.5 gm.

The mycelial solids (reserved above) were extracted 2 times, each time with one-half volume of methanol, and the extracts combined and concentrated to remove the methanol. The aqueous phase remaining was extracted twice with equal volumes of n-butanol saturated with water, and the aqueous layer was discarded. The n-butanol extracts were combined and concentrated in vacuo to an oil having a volume of about 1 liter. This oil was then taken up in 500 ml. of methanol. After thorough mixing, the material was filtered and the filtrate again concentrated in vacuo to an oil, which was taken up in 250 ml. of methanol, and the solution was filtered. The filtrate was poured into five liters (20 volumes) of isopropyl alcohol to induce precipitation. The active precipitate which formed was filtered off, washed with acetone, and dried in vacuo. It weighed 29.5 grams.

Further purification of the A-32724 complex and separation of the factors were accomplished using a silica-gel column. The column was prepared by slurrying grade 62 silica gel (Grace) with acetone. The silica gel was then packed in a column (15×150 cm., volume 10 L.) and washed with acetone. Antibiotic A-32724 complex, weighing 55 g., obtained as described above, was dried onto grade 62 silica gel from water, and added to the top of the previously prepared silica gel column. The column was eluted with acetone at a flow rate of about 350–400 ml./hr. Fractions of about 700–800 ml. each were collected every two hours. The fractions were evaluated by thin-layer chromatography (TLC) using vanillin-sulfuric acid spray. This spray produces a bright red spot with the several factors of antibiotic A-32724. On the basis of this spot test, Fractions 1–16, inclusive, were discarded. Fractions 17–22, inclusive, were combined and were determined to contain a mixture of Factor A and Factor B. On further standing and workup, there was obtained the desulfated compound corresponding to Factors A and B, and having a melting point of about 58° C. There was also obtained the desulfated and de-acetylated compound corresponding to Factors A and B, and having a melting point of about 99° C.

Fractions 23–34, inclusive, yielded impure Factor B. Fractions 35–114, inclusive, yielded degradation products. Fractions 115–226, inclusive, were discarded. Fractions 227–238, inclusive, yielded impure Factor A. Fractions 239–249, inclusive, yielded Factor C.

The eluant was changed to 1% water in acetone, and there was obtained impure Factor C.

EXAMPLE 3

Isolation of Factors A and B

An improved isolation of Factors A and B was accomplished according to the following procedure. Dry solid crude complex (43.3 g.), from Example 1, above, was refluxed overnight in methanol at a concentration of about 20 mg./ml. At the end of the reflux period, the mixture was filtered and the filtrate evaporated to dryness in vacuo. This procedure of refluxing the crude antibiotic complex in methanol served to transform factor C into factor A. The resulting solid was washed with acetone and benzene and dried in vacuo. The solid weighed 42.6 g. after drying.

A 1-g. portion of this dried material was dissolved in about 5 ml. of water. The solution was then dried onto about 10–15 g. of silica gel grade 62 in vacuo. This material was then added to the top of a 300 cc. column of silica-gel grade 62 prepared in ethyl acetate. A stepwise gradient of methanol in ethyl acetate was applied to the column. Factor A was eluted using 5% methanol in ethyl acetate. The composition of the eluting solvent was then changed, and factor B was eluted using 10% methanol in ethyl acetate. The presence of the factors in the fractions was determined by thin-layer chromatography using the vanillin-sulfuric acid spray. Factor A is distinguishable from Factor B because Factor A moves more rapidly than Factor B on silica gel in 2:1 methanol:chloroform.

EXAMPLE 4

Isolation of Factor C

Ten grams of antibiotic A-32724 complex (prepared as in Example 2, *supra*) was dissolved in water. The pH of the solution was adjusted to 8.5, and the solution was chromatographed on a polyamide (Polyamide Woelm for column chromatography) column (4.7×65 cm., volume 1 L.). Fractions, each 100 ml. in volume, were collected, and were monitored by the color of the fraction and the activity vs. *Staphylococcus aureus*. The first fractions were colored and negative vs. *S. aureus*. Fractions 1–20, inclusive, were discarded. Later fractions (21–29) were colored and positive vs. *S. aureus*. The last fractions (Fractions 30–40, inclusive) were uncolored and positive vs. *S. aureus*.

Fractions 21–29, inclusive, were combined and concentrated *in vacuo* to yield an oil. The oil was taken up in water and poured into 20 volumes of methanol. The precipitate which formed was filtered off and discarded. The filtrate was concentrated *in vacuo* to yield an oil, which oil was taken up in water and the solution which formed was poured into 3 volumes of n-propanol. A precipitate formed which was filtered off and discarded. The filtrate was concentrated *in vacuo* to an oil which was taken up in warm (about 40° C.) ethanol and allowed to stand at room temperature for some time. The crystals which separated were recovered by filtration, had a melting point of about 185°–186° C., and weighed 201 mg., and were identified by NMR, IR, and UV spectra as Factor C.

Fractions 30–40, inclusive, were treated in the same manner to give a product having a melting point of about 184°–186° C., weighing 210 mg., and identified as Factor C by NMR, IR, and UV spectra.

What is claimed is:

1. Antibiotic A-32724 Factor A having the following physical and chemical properties:
   (1) Melting point of about 175°–176° C. (dec.);
   (2) Molecular weight 738 (determined by nuclear magnetic resonance spectrum, sulfate determination, and field-desorption and electron-impact mass spectrometry);
   (3) Ultraviolet absorption spectrum in aqueous solution having absorption maxima at 265 nm ($\epsilon$=333), and 271 nm (sh) ($\epsilon$=252);
   (4) Infrared absorption spectrum shown in FIG. 1 as measured by KBr pellet method and having the following distinguishable absorption maxima: 3426 (strong), 2923 (strong), 2852 (strong), 1736 (medium), 1720 (medium), 1616 (medium), 1590 (medium), 1458 (medium), 1383 (shoulder), 1375 (medium weak), 1241 (very strong), 1123 (weak), 1068 (strong), 981 (strong), 884 (weak), 865 (weak), 625 (weak), and 581 cm.$^{-1}$ (weak);
   (5) Proton magnetic resonance spectrum in DMSO-$d_6$, at 100 MHz, using internal TMS as reference, as follows:

| Resonance Description | Chemical Shift δ, ppm | No. of Protons |
|---|---|---|
| Triplet | 6.80 | 1 |
| Doublet | 6.74 | 2 |
| Multiplet | 4.67 | 1 |
| Doublet | 4.60 | 1 (exchangeable) |
| Multiplet | 3.40 | 1 |
| Triplet | ~2.5 | Overlapped with solvent |
| Singlet | 1.97 | 3 |
| Multiplet | ~1.5 | 42 |
| Broad singlet | 1.23 | |
| Triplet | 0.84 | 3 |

(6) $^{13}C$ Nuclear magnetic resonance spectrum, in DMSO-$d_6$, using internal TMS as reference, showing chemical shifts, expressed in parts per million, as follows:

| No. | PPM |
|---|---|
| 1 | 170.0 |
| 2 | 153.4 |
| 3 | 142.7 |
| 4 | 115.1 |
| 5 | 110.4 |
| 6 | 75.8 |
| 7 | 70.8 |
| 8 | 35.2 |
| 9 | 32.2 |
| 10 | 31.2 |
| 11 | 30.9 |
| 12 | 29.3 |
| 13 | 29.0 |
| 14 | 28.7 |
| 15 | 28.5 |
| 16 | 25.1 |
| 17 | 25.0 |
| 18 | 22.1 |
| 19 | 20.8 |
| 20 | 13.9 |

(7) Solubility to solvent: Soluble in water and methanol;

(8) Color and form of substance: Amorphous white powder; and (9) An empirical formula of $C_{33}H_{56}O_{11}S_2Na_2$.

2. Antibiotic A-32724 Factor B having the following physical and chemical properties:

(1) Melting point of about 160°–162° C. (dec.);

(2) Molecular weight 738 (determined by nuclear magnetic resonance spectrum, sulfate determination, and field-desorption and electron-impact mass spectrometry);

(3) Ultraviolet absorption spectrum in water solution having absorption maxima at 265 nm ($\epsilon$=321), and 271 nm (sh) ($\epsilon$=249);

(4) Infrared absorption spectrum shown in FIG. 2 as measured by KBr pellet method and having the following distinguishable absorption maxima: 3468 (strong), 3452 (strong), 2923 (strong), 2853 (strong), 1733 (medium), 1616 (medium), 1591 (medium weak), 1455 (medium), 1376 (weak), 1242 (very strong), 1124 (weak), 1068 (strong), 1032 (shoulder), 980 (strong), 905 (weak), 795 (medium), 767 (medium weak), 721 (weak), 684 (weak), 670 (shoulder), 662 (shoulder), 617 (medium weak), and 579 cm.$^{-1}$ (medium);

(5) Proton magnetic resonance spectrum in DMSO-$d_6$, at 100 MHz, using internal TMS as reference, as follows:

| Resonance Description | Chemical Shift δ, ppm | No. of Protons |
|---|---|---|
| Triplet | 6.78 | 1 |
| Doublet | 6.73 | 2 |
| Multiplet | 4.95 | 1 |
| Multiplet | 4.08 | 1 |
| Triplet | ~2.5 | Overlapped with solvent |
| Singlet | 1.98 | 3 |
| Multiplet | ~1.5 | ~40 |
| Broad singlet | 1.23 | |
| Triplet | 0.85 | 3 |

(6) $^{13}C$ Nuclear magnetic resonance spectrum, in DMSO-$d_6$, using internal TMS as reference, showing chemical shifts, expressed in parts per million, as follows:

| No. | PPM |
|---|---|
| 1 | 169.8 |
| 2 | 153.4 |
| 3 | 142.7 |
| 4 | 115.1 |
| 5 | 110.3 |
| 6 | 75.9 |
| 7 | 72.8 |
| 8 | 62.9 |
| 9 | 41.1 |
| 10 | 40.2 |
| 11 | 39.4 |
| 12 | 33.5 |
| 13 | 37.7 |
| 14 | 35.2 |
| 15 | 31.2 |
| 16 | 30.8 |
| 17 | 29.9 |
| 18 | 29.0 |
| 19 | 25.0 |
| 20 | 24.5 |
| 21 | 22.0 |
| 22 | 20.7 |
| 23 | 13.9 |
| 24 | 0.0 |

(7) Solubility to solvent: Soluble in water and methanol;

(8) Color and form of substance: Amorphous white powder; and (9) An empirical formula of $C_{33}H_{56}O_{11}S_2Na_2$.

* * * * *